(12) United States Patent
Oellgaard et al.

(10) Patent No.: US 11,679,022 B2
(45) Date of Patent: Jun. 20, 2023

(54) OSTOMY BASE PLATE HAVING VALLEYS OF RELATIVELY LOWER ADHESIVE THICKNESS AND RIDGES OF RELATIVELY HIGHER ADHESIVE THICKNESS

(71) Applicant: Coloplast A/S, Humlebaek (DK)

(72) Inventors: Claus Oellgaard, Fredensborg (DK); Niels Pinholt, Roskilde (DK)

(73) Assignee: Coloplast A/S, Humlebaek (DK)

( * ) Notice: Subject to any disclaimer, the term of this patent is extended or adjusted under 35 U.S.C. 154(b) by 139 days.

(21) Appl. No.: 17/394,486

(22) Filed: Aug. 5, 2021

(65) Prior Publication Data

US 2021/0361468 A1    Nov. 25, 2021

Related U.S. Application Data (63) Continuation of application No. 15/758,728, filed as application No. PCT/DK2016/050297 on Sep. 9, 2016, now Pat. No. 11,109,997.

(30) Foreign Application Priority Data

Sep. 11, 2015   (DK) ............................ PA 2015 70585

(51) Int. Cl.
*A61F 5/445*   (2006.01)
*A61F 5/443*   (2006.01)
*A61F 5/44*    (2006.01)
*A61F 5/448*   (2006.01)

(52) U.S. Cl.
CPC .............. *A61F 5/445* (2013.01); *A61F 5/443* (2013.01); *A61F 5/4404* (2013.01); *A61F 2005/4483* (2013.01)

(58) Field of Classification Search
CPC ........ A61F 5/445; A61F 5/4404; A61F 5/443; A61F 2005/448
See application file for complete search history.

(56) References Cited

U.S. PATENT DOCUMENTS

| | | | |
|---|---|---|---|
| 3,076,458 A | 2/1963 | Mason | |
| 4,872,464 A | 10/1989 | Loeb et al. | |
| 5,704,905 A * | 1/1998 | Jensen | A61F 13/025 602/42 |
| 6,039,714 A * | 3/2000 | Cracauer | A61J 15/0038 604/174 |
| 7,049,478 B1 * | 5/2006 | Smith | A61F 13/067 128/892 |
| 7,586,019 B2 * | 9/2009 | Oelund | A61F 5/448 602/41 |
| 8,211,073 B2 * | 7/2012 | Dove | A61F 5/445 604/338 |

(Continued)

FOREIGN PATENT DOCUMENTS

| | | |
|---|---|---|
| CN | 102655827 A | 9/2012 |
| EP | 324511 A2 | 7/1989 |

(Continued)

*Primary Examiner* — Guy K Townsend
(74) *Attorney, Agent, or Firm* — Coloplast Corp., Coloplast A/S; Nick Baumann (57) ABSTRACT

An ostomy base plate has undulations formed in an adhesive composition to provide the adhesive composition with valleys of relatively lower adhesive thickness and ridges of relatively higher adhesive thickness.

13 Claims, 2 Drawing Sheets

(56) References Cited

U.S. PATENT DOCUMENTS

| | | | | |
|---|---|---|---|---|
| 8,399,732 B2* | 3/2013 | Oelund | A61F 5/448 | |
| | | | 602/41 | |
| 8,672,908 B2* | 3/2014 | Todd | A61F 5/445 | |
| | | | 604/338 | |
| 8,708,987 B2* | 4/2014 | Cramer | A61F 5/443 | |
| | | | 604/344 | |
| 8,951,237 B2* | 2/2015 | Nordby | A61L 24/043 | |
| | | | 604/336 | |
| 9,066,812 B2* | 6/2015 | Edvardsen | A61F 5/443 | |
| 9,289,322 B2* | 3/2016 | Lam | A61L 24/046 | |
| 9,622,903 B2* | 4/2017 | Israelson | A61F 5/448 | |
| 9,770,359 B2* | 9/2017 | Edvardsen | A61F 5/445 | |
| 9,980,849 B2* | 5/2018 | Lam | A61L 24/001 | |
| 10,517,754 B2* | 12/2019 | Praame | A61F 5/443 | |
| 10,881,546 B2* | 1/2021 | Hansen | A61F 5/445 | |
| 11,033,418 B2* | 6/2021 | O'Brien | A61F 5/443 | |
| 11,051,969 B2* | 7/2021 | Nyberg | A61F 5/445 | |
| 11,109,997 B2* | 9/2021 | Oellgaard | A61F 5/4404 | |
| 2005/0054997 A1* | 3/2005 | Buglino | A61F 5/448 | |
| | | | 604/332 | |
| 2006/0195053 A1* | 8/2006 | Oelund | A61F 5/443 | |
| | | | 602/42 | |
| 2008/0038536 A1* | 2/2008 | Strobech | C09J 7/20 | |
| | | | 427/208.4 | |
| 2010/0022933 A1* | 1/2010 | Oelund | A61F 5/443 | |
| | | | 604/338 | |
| 2010/0324511 A1* | 12/2010 | Dove | A61F 5/445 | |
| | | | 604/338 | |
| 2012/0041404 A1* | 2/2012 | Bach | A61F 5/443 | |
| | | | 604/344 | |
| 2012/0323192 A1* | 12/2012 | Willoughby | A61F 5/445 | |
| | | | 604/337 | |
| 2013/0138063 A1* | 5/2013 | Wiltshire | A61F 13/0246 | |
| | | | 604/344 | |
| 2013/0226116 A1* | 8/2013 | Edvardsen | A61F 5/443 | |
| | | | 604/338 | |
| 2013/0226117 A1* | 8/2013 | Hansen | A61L 24/0036 | |
| | | | 604/338 | |
| 2013/0274696 A1* | 10/2013 | Lam | A61L 24/046 | |
| | | | 604/332 | |
| 2014/0114265 A1* | 4/2014 | Israelson | A61F 5/443 | |
| | | | 604/342 | |
| 2014/0323941 A1* | 10/2014 | Lee | C09J 7/22 | |
| | | | 428/137 | |
| 2015/0297389 A1* | 10/2015 | Nyberg | A61F 5/443 | |
| | | | 604/344 | |
| 2016/0158057 A1* | 6/2016 | Lam | A61L 24/001 | |
| | | | 604/338 | |
| 2017/0143535 A1* | 5/2017 | Praame | A61F 5/443 | |
| 2017/0224523 A1* | 8/2017 | Bendix | A61F 5/445 | |
| 2018/0021164 A1* | 1/2018 | Fenton | A61F 13/02 | |
| | | | 604/336 | |
| 2018/0021165 A1* | 1/2018 | Fenton | A61F 5/445 | |
| | | | 604/338 | |
| 2018/0104089 A1* | 4/2018 | Nyberg | A61F 5/445 | |
| 2018/0235801 A1* | 8/2018 | Oellgaard | A61F 5/445 | |
| 2018/0296384 A1* | 10/2018 | O'Brien | A61F 5/443 | |
| 2021/0113362 A1* | 4/2021 | Windeballe | A61F 5/0043 | |
| 2021/0361468 A1* | 11/2021 | Oellgaard | A61F 5/443 | |

FOREIGN PATENT DOCUMENTS

| | | |
|---|---|---|
| EP | 0882437 A2 | 12/1998 |
| EP | 2651350 B1 | 11/2015 |
| GB | 2311467 A1 | 10/1997 |
| JP | 2006296634 A | 11/2006 |
| JP | 2013116310 A | 6/2013 |
| WO | 9300056 A1 | 1/1993 |
| WO | 9853771 A1 | 12/1998 |
| WO | 9936017 A1 | 7/1999 |
| WO | 2005048892 A2 | 6/2005 |
| WO | 2009023870 A1 | 2/2009 |
| WO | 2010008385 A1 | 1/2010 |
| WO | 2013000482 A1 | 1/2013 |
| WO | 2013083689 A1 | 6/2013 |
| WO | 2014086369 A1 | 6/2014 |
| WO | 2014117778 A1 | 8/2014 |
| WO | 2015090332 A1 | 6/2015 |
| WO | 15180732 A1 | 12/2015 |

* cited by examiner

OSTOMY BASE PLATE HAVING VALLEYS OF RELATIVELY LOWER ADHESIVE THICKNESS AND RIDGES OF RELATIVELY HIGHER ADHESIVE THICKNESS

Disclosed is an adaptable ostomy base plate for attachment to a skin surface of a user and a collecting bag connected to the adhesive base plate. The adaptable base plate includes a top film, an adhesive composition, and at least one release liner.

DETAILED DESCRIPTION

Embodiments provide an adaptable ostomy base plate according to the appended claims.

Some definitions regarding the subject matter of the attached claims are presented below.

When referring to the proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction, or axially, is defined as the direction of the stoma when the appliance is worn by a user. Thus, the axial direction is substantially perpendicular to the abdominal surface of the user.

The radial direction, or radially, is defined as transverse to the axial direction that is transversely to the direction of the stoma.

An "adaptable ostomy base plate" is intended to define that at least a part of the ostomy base plate can change its form or shape by an intended interaction of a user or health care professional.

A "flexible top film" is intended to define a film material carrying or having disposed thereon, adhesive material to make the product adhere to the skin of a user and that the top film material does not break or become weaker even at very high elongation or stretching rates. A flexible top film is further defined below.

An "elastic skin-friendly adhesive" is intended to define an adhesive material having a low risk of irritating the skin of a user and that the adhesive material is capable of following the elongations and relaxations of the flexible top film without breaking or substantially changing characteristics. An elastic skin-friendly adhesive is further defined below.

An "adhesive base plate" is intended to define a top film coated on the proximal surface with a skin-friendly adhesive.

A "substantially convex shape" is intended to define that an element or its corresponding surface has a shape or form that provides an overall convexity. In other words, while a smaller section or zone making up part of the overall element or its corresponding surface may have e.g. a linear shape or form, the element or surface as a whole has a convex shape. It is of course to be understood that if for a sheet- or plate-like element one major surface has a convex shape, the opposite major surface may necessarily have a corresponding concave shape. However, for clarification purposes only, and in relation to the present application, "convex" may preferably refer to the proximal side and "concave" to the distal side as both defined above.

Similarly, a "substantially concave shape" is intended to define that an element or its corresponding surface has a shape or form that provides an overall concavity.

"Initial engagement" is intended to define the first contact between the ostomy base plate and the skin surface of the user in the process of applying the product; however not meaning that the ostomy base plate is fully and functionally correct attached to the skin surface.

"Permanent engagement" is intended to define the engagement or attachment of the ostomy base plate when the application process is completed and the ostomy base plate is fully and functionally correct attached to the skin surface. However, it should be understood that permanent engagement is only intended to mean for the normal life- or wear time of the ostomy base plate.

"Release liner" is intended to define a liner covering the proximal (skin contacting) side of the skin-friendly adhesive, that ensures at least that the properties of the adhesive are preserved and that the adhesive surface is not laid open until just before use.

"Fittingly engage" is intended to define that the attachment between the ostomy base plate and the skin surface is as good as possibly feasible and at least with no or only insignificant creases or folds on the proximal surface of the base plate.

"Peristomal skin surface" is intended to define an area of the skin surface adjacent to and surrounding the stoma. The extent of the area may be considered to correspond approximately to a skin surface area covered by at least a first section of the ostomy base plate—the first section then being closer to the stoma than a second section.

"Invertible" is intended to define that the at least first and/or second section provides little or no resistance to being shifted from a substantially convex shape to a substantially concave shape, or vice versa, by a movement involving no sudden switching or "flipping-over" of the section (i.e. as it is known from a bi-stable construction which may change shape when a certain force-threshold is reached).

"Store configuration" is intended to describe the position of the base plate before application is completed. The base plate is stable in this configuration and can be stored in this configuration. In the initial steps of application, the base plate may be in store configuration.

"Use configuration" is intended to describe the position of the base plate after application is completed, and is the inverted configuration of the store configuration.

Embodiments provide an adaptable ostomy base plate comprising a flexible top film, the base plate having a first section and a second section, and having at least a first elastic skin-friendly adhesive on a proximal surface of said flexible top film, a stoma-receiving through-going hole defining an inner boundary of said first section, said first section being adjacent to and extending radially from said through-going hole and said second section surrounding said first section, an outer boundary of the second section defining an outer boundary of the base plate, and one or more release liners, the base plate having a substantially convex shape for initial engagement with a peristomal skin surface and configured to be invertible to a substantially concave shape to fittingly engage to a topography of the peristomal skin surface for permanent engagement thereto, the base plate comprising a reinforcement ring arranged on a distal surface of the flexible top film between the inner boundary and the outer boundary, and wherein the first section comprises a series of concentric undulations, provided in a radial extent of the distal surface of the base plate from the inner boundary to a position under the reinforcement ring.

In one embodiment, the distal surface of the base plate includes a series of concentric undulations. In one embodiment, the undulations are in the form of a series of valley and ridges. In one embodiment, undulations are provided as embossments in the base plate, wherein the flexible top film is formed and the adhesive layer is formed to follow the undulations of the flexible top film. In one embodiment, the adhesive layer of the base plate is formed into valleys of a relatively lower thickness and ridges of a relatively higher thickness. The thickness of the adhesive layer is measured perpendicular to the skin facing surface of the adhesive layer as the distance from the skin facing (proximal) surface of the adhesive layer to the proximal surface of the flexible top film. It is to be understood that the skin facing (proximal) surface of the adhesive layer is a generally even surface, i.e. the skin facing surface of the adhesive layer does not undulate. In embodiments, the undulations are provided continuously over an entirety of the first section or over only a portion of the first section. In one embodiment, the undulations are formed in a homogenous pattern. In one embodiment, the undulations are located in discrete areas of the first section. In embodiments, undulations are provided in an area of the flexible top film extending at least partially under a reinforcement ring and the radially inward extending area next to the ring.

In embodiments, the concentric undulations are defined by a series of concentric ridges and valleys progressing radially outwardly from the stoma-receiving through-going hole towards the reinforcement ring. In embodiment, the concentric ridges and valleys are substantially circular or they correspond to a geometry of an outer perimeter of the base plate or to a geometry of the reinforcement ring, such as oval shaped, star shaped, square shaped or other geometric configurations.

In embodiments, the distance between the ridges may be 1-3 mm, such as 1-2 mm such as 1.5-2 mm, the distance being measured radially from a centre of a ridge to the centre of the neighbouring ridge. The thickness of the adhesive layer at the ridges may be 1-6 mm, such as 1-4 mm such as 1-2 mm or even 1.2-1.8 mm. The thickness of the adhesive layer in the valleys may be 5-90%, such as 10-85%, such as 15-80%, such as 20-80% or even around 70% of the thickness of the adhesive layer at the ridges.

The disclosed base plate is configured to be invertible during application to the peristomal skin surface around a protruding stoma. By such inversion, the flexible top film tends to plastically deform and the adhesive layer tend to become compacted.

According to embodiments of the present disclosure, the undulations of the first section allows the flexible top film to be sufficiently extendible ("stretched") when the base plate is inverted during application to the peristomal skin surface. Moreover, the relatively lower thickness of the adhesive layer in the valleys reduces the tendency to compacting of the adhesive. This reduces or eliminates undesirable "lifting" of the base plate adjacent the inner boundary, which could eventually lead to detachment of the base plate from the skin surface. In other words, one effect of the undulations is that the flexible top film does not pull the adhesive away from the skin when the base plate is inverted, as the ridges and valleys provide more top film together with a more flexible adhesive construction due to the thinner layer.

The ridges and valleys at the first section being the part of the base plate located between the reinforcement ring and the through going hole enables the top film and the adhesive to stretch and compact more easily and allow the base plate to follow the contour of the skin after inverting the base plate to attachment on the user's skin.

In embodiments, an area under the reinforcement ring is provided with undulations. The undulations may be in the form of one or more ridges and valleys or it may be one lower ridge extending over the entire area. In embodiments, a lower ridge under the reinforcement ring has a width (measured in radial direction) larger than the width of the reinforcement ring. The lower ridge under the ring may have a width essentially corresponding to or being wider than the ring. The undulations under the ring and close to the fixation point of the ring along the outer periphery of the ring to the top film may work as a hinge for the reinforcement ring to pivot around thereby avoiding the first section to turn upwards after inversion of the base plate.

In embodiments, the lower ridge may have a thickness being 80-95%, such as 86-92% of the thickness of the adhesive layer of the ridges.

In embodiments, the undulations comprise at least two ridges and two valleys.

In embodiment, an outer boundary of the base plate is defined by an outer boundary of the second portion.

In embodiments, the second section of the base plate comprises radially extending petals, the petals being interconnected by less radially extending bridges. Thus, in embodiments, the perimeter of the base plate is star shaped or flower shaped. In embodiments, the base plate comprises at least three petals, such as four petals, such as five petal or even such as six petals.

In embodiments, the petals may be equidistantly spaced apart around the circumference of the central part.

The petals facilitate "tailor fitting" of the base plate to bulgy peristomal skin surfaces by having fewer folds and wrinkles compared to a base plate without petals.

In embodiments, a peripheral portion of the base plate adjacent to the outer periphery is provided with embossed lines. In embodiments, the embossed lines are located at sections of the outer periphery such as at the bridges or petals. In embodiments, the embossed lines are applied along an entire outer periphery of the base plate. The embossed lines provide increased flexibility to the base plate as well as reducing folds and wrinkles of the peripheral portion of the base plate. In embodiments, the embossed lines are located where folding lines, by experience, usually or naturally occur, thereby absorbing forces of the folding lines.

In embodiments, the base plate is provided with at least one release liner for protecting the proximal adhesive surface before application. The release liner may be form stable and able to stabilize and fix the concave contour of the base plate. Due to the elasticity of the base plate, in embodiments, it is advantageous to have a release liner being stiff enough to be able to keep the base plate in its convex shape until application.

In embodiments, the release liner is produced from a material that can be thermo formed. The release liner may have a stiffness being higher than the stiffness of the combined top film and adhesive layer. The release liner may have a thickness of 0.10 to 0.20 mm, more preferred 0.15 mm. The release liner may have a thickness of 0.15 mm.

The at least one release liner used in connection with the ostomy base plate may suitably be a siliconised or fluorinated liner, such as a siliconised or fluorinated craft paper, polyethylene, polypropylene or polyethylene terephthalate film.

In embodiment, the adaptable base plate is provided with a collection bag. The collection bag may be attached permanently to the base plate or it may be detachable.

In embodiments, the ostomy base plate is provided with coupling means for attachment of a collection bag. The coupling means may be in the form of a mechanical coupling or it may be an adhesive coupling.

The reinforcement ring facilitates the adaptable base plate to maintain and stabilize the convex shape of the base plate when the release liner is removed.

In embodiments, the reinforcement ring is positioned at a radial distance from the stoma receiving opening of 0-60%, such as 0-50% of the radial distance from the inner boundary to the outer radial boundary, or more specifically between 1-40% of the radial distance from the inner boundary to the outer radial boundary, or even more specifically between 2-30% of the radial distance from the inner boundary to the outer radial boundary, or especially between 5-20% of the radial distance from the inner boundary to the outer radial boundary. The outer radial boundary is herein defined as the shortest radius measured of the outer boundary of the base plate, being at the bridges in case the base plate is provided with petals. The reinforcing ring defines the boundary between the first section and the second section of the base plate.

In embodiments, the reinforcement ring is made of a material that is more rigid than the adhesive layer and/or the top film. In embodiments, the reinforcement ring is made of a thermoplastic material.

In embodiments, the reinforcement ring is made of a material that provides a greater rigidity along the radial axis than the adhesive and/or top film of the ostomy base plate. In embodiments, the reinforcement ring is made of a material that provides a greater rigidity along the axial direction than the adhesive and/or top films of the ostomy base plate.

In embodiments, the reinforcement ring facilitates that the base plate is stabilized in a convex shape when the release liner is removed.

In embodiments, a width of the reinforcement ring is approximately 5-7 mm such 5-7 mm, such as 5.5 mm. In embodiments relating to a two-piece ostomy appliance, the reinforcement ring can be combined with a coupling for attachment of a collection bag. In such embodiments, the width of the reinforcement ring is made broader, up to 11 mm.

The reinforcement ring may be attached to the top film along its outer periphery, allowing the adhesive wafer to stretch and compact more freely under the ring.

The concave/convex shape of the base plate may be a section of a sphere. This facilitates easy fitting to a protruding stoma. The curvature of the central portion of the base plate may fit to the curved body part and the petals along the outer boundary may allow tailor fit to the peripheral area of the body part. In embodiments, at least a part of the first section of the base plate may be substantially planar.

In a first aspect, a number of advantageous effects are achieved. First, a user having a stoma located on a bulge or hernia, or on an otherwise "hilly" topographic skin surface, has improved control of the product application procedure.

This effect is at least partly achieved in the following manner: subsequent to removal of at least one release liner covering at least partly the first section, the user engages a part of the first section immediately adjacent to the stoma-receiving through-going hole with the peristomal skin surface, whereby only a small area of the adhesive on the proximal surface of the flexible top film is engaged with the peristomal skin surface.

Thereby, the user is provided with the opportunity to correct the positioning of the ostomy base plate to a more suitable position in case of misalignment of the initial engagement without having engaged the whole of the proximal adhesive surface of the flexible top film with the skin surface. This may be particularly advantageous in cases where the user has limited or no visual contact with the stoma.

Furthermore, since at least the first section has a first substantially flat or convex shape, a user reaching down to the stoma located on the bulge or hernia in order to apply the product will have improved tactile and/or visual contact with the stoma and/or the peristomal area. This is because the part of the first section not initially engaging the peristomal skin surface extends away from the skin surface, thus leaving some space between the base plate and the skin, giving room for one or more of the user's fingers, and thereby the first section also does not block or impede possible visual contact for correct positioning of the base plate in relation to the stoma.

Once the initial engagement of the first section is effected, the base plate is inverted by the user to a substantially concave shape to fittingly engage the first and the second section to the peristomal skin surface on the bulge or hernia.

According to the present disclosure, the adhesive proximal side of the first section will adapt smoothly to the topography of the peristomal skin surface when the user applies a gentle pressure to the distal surface of the first section.

This may advantageously, but not exclusively, be done by the user letting his finger or fingers describe one or more radial motions by placing the finger(s) immediately to adjacent the stoma, providing pressure to the distal surface, and sliding the finger gently across the distal surface of the first section radially away from the stoma. Alternatively, the adaptation may be done by a motion placing a finger immediately to adjacent the stoma, providing pressure to the distal surface, and sliding the finger gently in a "spiral-like" pattern gradually away from the stoma over the entire distal surface of the first section.

However, regardless of the way of adaptation, at least the flexibility of the flexible top film and the elasticity of the skin-friendly adhesive along with the planar or convex shape of the first section make the fitting engagement of the first section possible.

As can be understood from the above, the flexible top film and the elastic skin-friendly adhesive facilitate the inversion of the first section for application to the peristomal skin surface by a continuous, regular movement. This provides a user with improved control of the application procedure. This should be seen in contrast to a sudden movement which would be the case e.g. in the case of a bi-stable construction, i.e. a construction having one predetermined position where it changes shape from one form to another, e.g. from convex to concave.

The flexible top film according to the invention may be a blown film primarily based on one or more Ethylene Vinyl Acetate (EVA) materials, one or more thermoplastic polyurethane elastomer (TPU) based materials and one or more polyethylene (PE) materials.

Particularly, but not exclusively, the EVA and TPU based materials may provide a good basis for engagement of the top film with other elements of the ostomy base plate such as the adhesive(s) and optional first coupling means, or in the case of the base plate being used for a one-piece ostomy appliance, with the material of the collecting bag for human body wastes. The PE material(s) may particularly, but not exclusively, provide a suitable basis for shaping the flexible top film into a convex or concave shape to be able to fittingly engage with a topography of a user's skin surface.

In embodiments, the flexible top film is a three-layer laminate.

Particularly, but not exclusively, the flexible top film may be made as a laminate comprising three individual (blown) layers each of which is made from either EVA, TPU or PE or from a blend of these. The three layers may be blown simultaneously. In the three-layer laminate, the distal-most (with reference to the use situation of the ostomy base plate) layer may be made from a blend of Elvax® 3190, an EVA material from DuPont, and Orevac® 18360, a PE material from Arkema; the middle layer may be made from a blend of Elvax® 3190, Elastollan® 890, a TPU-Polyester material from BASF and Elastollan® 978, another TPU-Polyester material from BASF and; the proximal layer may also be made from a blend of Elvax® 3190, Elastollan® 890 and Elastollan® 978. In addition to these components each of the distal and proximal layers of the three-layer laminate may also comprise a minor amount of slip agent (to assist when unrolling the top film material for production of the ostomy base plate). The slip agent may be a PE/EVA polymer carrier containing silica, oleamid (fatty acid oleic acid) and erucamide (monounsaturated omega-9 fatty acid), such as Polystatic® 90200-2. The silica and the ole-/erucamides in the slip agent provide the slipping effect.

The overall thickness of the flexible top film may be in a range of 30-70 μm, such as 35-50 μm, such as approximately 40 μm. In embodiments of the three-layer laminate, each individual layer may have a thickness of at least 10 μm for ease of production of the individual layers.

The flexible top film may have a flexibility measured as a percentage of elongation of the flexible top film material before it fails (considered as the point where plastic deformation of the flexible top film occurs). The flexible top film may be 250-700% elongatable, such as 300-600% elongatable, such as 350-450% elongatable, such as 400% elongatable before failure.

The elastic skin-friendly adhesive layer may comprise one or more adhesive layers.

The first elastic skin-friendly adhesive according to the invention may be any pressure sensitive adhesive composition suitable for medical purposes. It may comprise a rubbery elastomeric base and one or more water soluble or water swellable hydrocolloids, the adhesive composition comprising a substantially homogeneous mixture of 25-60% of one or more polyisobutylenes, 3-35% of one or more styrene copolymers, and 20-60% of one or more hydrocolloids, wherein the percentage by weight of one or more polyisobutylenes and one or more styrene copolymers and one or more hydrocolloids add up to 100% by weight of the adhesive composition. For further information on such compositions, reference is made to applicant's granted European patent EP1541180B1.

In embodiments, the first skin-friendly adhesive is elastic. This means that the first skin-friendly adhesive has elastic properties.

The thickness of the first elastic skin-friendly adhesive layer may be in a range of 0.8-2 mm, corresponding to 800 μm-2000 μm, such as 1000 μm-1800 μm, such as 1200 μm-1600 m.

For the production of the ostomy base plate, the following is an example of manufacture:

first the adhesive(s) is/are provided on the proximal surface of the flexible top film and thereafter the at least one release liner is provided on the adhesive surface, providing a planar laminate blank. At least the first section of the planar laminate blank is then subsequently placed in a vacuum-forming machine, the moulding tool having the relevant form such as a planar first section and a convex second section. Heating means, such as a radiant heat source is placed in connection with the vacuum-forming machine in order to soften the laminate blank, and the laminate blank is subjected to heat and vacuum forming for an adequate holding time. Alternatively, the laminate blank may also be manufactured by means of a heat and pressure die or indeed any other suitable procedure.

Due to its elasticity, the first skin-friendly adhesive may easily adapt to the desired shape of the first and the second section together with the flexible top film and the at least one release liner in the shaping process. Indeed, subjected to the above described shaping process, at least the second section of the ostomy base plate according to the invention initially always has the convex shape notwithstanding its high degree of adaptability. As mentioned, this may be seen in contrast to e.g. the known bi-stable convex ostomy products that are relatively rigid and only adaptable in an "either inverted/not inverted" sense.

The second section may be permanently engaged to the skin surface of the user by fitting the peripheral portion of the second section, such as fitting each petal to the skin. The engagement of the second section to the skin surface may be carried out after the first section has been permanently engaged with the peristomal skin surface.

The second section surrounds the first section of the adaptable ostomy base plate.

In embodiments, the adaptable ostomy base plate comprises a second skin-friendly adhesive.

The second skin-friendly adhesive may be provided to give a section of the base plate different characteristics and/or effects. As an example, the second skin-friendly adhesive may comprise smaller or a larger amount of a moisture absorbing component such as hydrocolloids and/or be more or less adaptable than the first skin-friendly adhesive. The second skin-friendly adhesive may be provided in a single or in multiple zones or areas. The zones or areas may have particular suitable shapes or forms depending on the function or effect of the second skin-friendly adhesive.

In embodiments, the second skin-friendly adhesive is provided on the first section.

This disposition of the first and second skin-friendly adhesive effectively provides an ostomy base plate, wherein the second skin-friendly adhesive having one set of characteristics covers the peristomal area, and the first skin-friendly adhesive having another set of characteristics covers the skin surface around (radially beyond) the peristomal skin surface.

In embodiments, the second skin-friendly adhesive is elastic. This means that in addition to the first elastic skin-friendly adhesive, also the second skin-friendly adhesive has elastic properties. The second skin-friendly adhesive may be more or may be less elastic than the first elastic skin-friendly adhesive or the two adhesives may even have identical elasticities if desired.

Where the elasticity of a construction is typically measured by the tensile elasticity Modulus (E) (also known as Young's Modulus) the elasticity of an adhesive is typically measured by the shear Modulus (G).

The shear Modulus of a viscoelastic material like an adhesive can be divided into a viscous part called the Loss Modulus (G") and an elastic part called the Storage Modulus (G'). The elastic response of the adhesives can therefore be measured by measuring G' by dynamic mechanical analysis (DMA), which is a well-known and established procedure to a skilled person working in the field of adhesives.

Body movements according to normal daily life routines typically occur at frequencies around 1-10 Hz. At these frequencies, the G' of the first elastic skin-friendly adhesive may be in a range from 850-1200 MPa, whereas G' of the second elastic skin-friendly adhesive may be in a range from 40-80 MPa.

In embodiments, the second elastic skin-friendly adhesive comprises a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1N).

Polymers that may be used for the second skin-friendly adhesive will generally be copolymers of ethylene and a polar monomer. The copolymers typically comprise less than about 70% ethylene, have water vapour transmission of more than 50 g/m2/day and a melt flow index of less than 2 g/10 min (190° C./21.1N). The melt flow index can be measured by the methods given in ISO 1133 and ASTM D1238. Examples of such polymers are copolymers of ethylene and vinyl acetate and copolymers of ethylene and butyl acrylate. Particularly preferred is ethylene and vinyl acetate copolymers with more than about 40% (w/w) vinyl acetate, a melt flow index of less than 2 g/10 min (190° C./21.1N), and a water vapour transmission of more than 50 g/m2/day for a 150 µm sheet when measured according to MVTR Test Method (inverted cup method).

Further information on the types of adhesives suitable for the second skin-friendly adhesive is disclosed in these embodiments, is available in applicant's published application WO 2009/006901A1.

In embodiments, the thickness of the second elastic skin-friendly adhesive is 300-700 µ-m, such as 550-650 µm, such as 600 µm.

In embodiments, the adhesive base plate will have a proximal ("skin-facing") surface, which faces the skin of the user during use, and a distal ("non-skin-facing") surface, which faces away from the user's skin during use. Before use, the proximal surface of the adhesive base plate can be covered by a release liner, which is releasably attached to the adhesive. The release liner can be removed by the user immediately prior to application of the adhesive base plate to the skin. Both before and during use, the distal surface of the adhesive base plate can be made up of a top film, which can be used to attach the collecting bag to the adhesive base plate, for instance by welding.

The adhesive base plate may include an absorbent adhesive composition. The absorbent adhesive composition is capable of absorbing moisture. The purpose of having an absorbent adhesive composition as a part of an ostomy device is to allow the absorbent adhesive composition to absorb moisture produced by the skin and thereby prevent accumulation of moisture at the skin surface, underneath the ostomy device. Accumulation of moisture on the skin surface can lead to damage of the skin, such as maceration.

In an aspect, the invention relates to an ostomy appliance comprising a collection bag and an adaptable ostomy base plate where the collection bag is detachable from the base plate.

In an aspect, the invention relates to an ostomy appliance comprising a collection bag and an adaptable ostomy base plate where the collection bag is integrated with the base.

In embodiments, the second absorbent adhesive composition is located only in the first section of the adhesive base plate. The absorbent adhesive composition may be located as a substantially ring-shaped element in the first section of the adhesive base plate, thus surrounding the stoma during use. A non- or less absorbing first adhesive may be located between the top film and the second adhesive and extend radially to cover the second section of the base plate.

The release liner may be of any material known to be useful as a release liner for medical devices. For instance, the release liner may be in the form of a polymer film, foil, or paper, having release properties that enable the adhesive to be released easily from the liner. Such properties may be inherent in the material or the layer may be siliconized, coated with a low surface tension coating, or subjected to other appropriate surface modifications. Release liners are in general made on a mechanically stiff backing such as polyethylene, polypropylene, or polyethylene terephthalate. This stiffness will support the adhesive base plate when applying the collecting device.

In embodiments, the second absorbent adhesive composition is in the form of a ring-shaped adhesive element located around the hole in the adhesive base plate and in contact with the release liner. Such a ring-shaped absorbent adhesive element could have a diameter of 30-70 mm, such as 40-70 mm, such as 50-70 mm, such as 60-70 mm. The ring-shaped adhesive element could for instance have a diameter of 30 mm, 40 mm, 50 mm, 60 mm, or 70 mm. The ring shaped element could have a width, i.e. the distance from the inner rim of the ring to the outer rim of the ring measured along the surface of the ring, of at least 10 mm, at least 20 mm, at least 30 mm, at least 40 mm, at least 50 mm, 10-20 mm, 10-30 mm, 10-50 mm, 20-30 mm, 20-40 mm, 20-50 mm, 30-40 mm, 30-50 mm, or 40-50 mm. The width of the element can be constant over the entire element or it may vary.

An adhesive element could also have an only roughly ring-shaped, oval, or roughly oval form. In that case, the mentioned diameters would be the maximum distance from one point on the outer edge of the element to another point on the outer edge of the element.

In embodiments, the second absorbent adhesive composition comprises a polymer comprising monomer units selected from the group consisting of styrene, isoprene, butadiene, ethylene, and butylene.

In embodiments, the second absorbent adhesive composition comprises a styrene block co-polymer.

In embodiments, the second absorbent adhesive composition comprises a styrene block co-polymer selected from the group consisting of styrene-isoprene-styrene (SIS), styrene-butadiene-styrene (SBS), styrene-isobutylene-styrene (SIBS), and styrene-ethylene/butylene-styrene (SEBS).

In embodiments, the second absorbent adhesive composition comprises a polyethylene copolymer.

In embodiments, the second absorbent adhesive composition comprises a polyethylene copolymer selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

In embodiments, the second absorbent adhesive composition comprises polyisobutylene (PIB).

In embodiments, the second absorbent adhesive composition comprises absorbent material selected from the group consisting of hydrocolloids, microcolloids, salt, and super absorbent particles.

In embodiments, the absorbent adhesive composition comprises an absorbent material in an amount of 1-60% (w/w) of the composition.

For instance, the absorbent adhesive composition comprises an absorbent material in an amount of 1-40% (w/w) or 1-20% (w/w) or 20-40% (w/w) or 20-60% (w/w) or 40-60% (w/w) or 25-50% (w/w) of the composition.

In embodiments, the absorbent material is selected from hydrocolloid, water soluble salt, mono, di- and oligosaccharides, sugar alcohols, polypeptides, organic acids, inorganic acids, amino acids, amines, urea, super absorbent particles such as polyacrylic acid, glycols such as polyethylene glycol, fumed silica, bentone, bentonite, and mixtures thereof.

In embodiments, the hydrocolloid is selected from guar gum, locust bean gum, pectin, potato starch, alginates, gelatine, xanthan or gum karaya, cellulose derivatives, salts of carboxymethyl cellulose, sodium carboxymethyl cellulose, methyl cellulose, hydroxypropyl cellulose, hydroxyethyl cellulose, sodium starch glycolate, polyvinylalcohol, and mixtures thereof.

In embodiments, the water soluble salt is selected from $NaCl$, $CaCl_2$, $K_2SO_4$, $NaHCO_3$, $Na_2CO_3$, $KCl$, $NaBr$, $NaI$, $KI$, $NH_4Cl$, $AlCl_3$, $CH_3COONa$, $CH_3COOK$, $HCOONa$, $HCOOK$, and mixtures thereof.

In embodiments, the switchable and/or the absorbent adhesive composition may comprise ingredients such as tackifiers, extenders, non-reactive polymers, oils (e.g. polypropyleneoxide, ethyleneoxide-propyleneoxide copolymers, mineral oil), plasticizers, fillers, and surfactants.

DETAILED DESCRIPTION OF THE DRAWINGS

Figure 1:
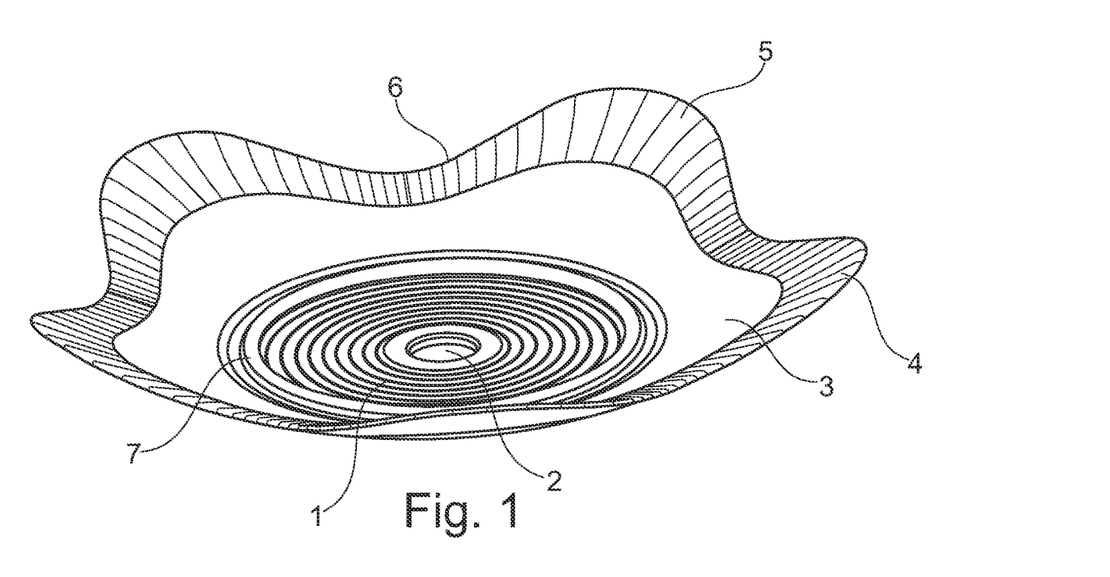
In FIG. 1 is shown one embodiment of an adaptable base plate.

In FIG. 1 is shown a top view of an embodiment of the adaptable base plate, the plate comprising a first central section 1 surrounding a hole 2 for accommodating a stoma, and a second peripheral section 3, the peripheral section being provided with embossed lines at the outer boundary 4. The outer boundary of the plate is defined by radially extending petals 5 interconnected by bridges 6. At the transition from the first section 1 to the second section 3 is located a reinforcement ring 7. The first section comprises concentric undulations surrounding the hole.

Figure 2:
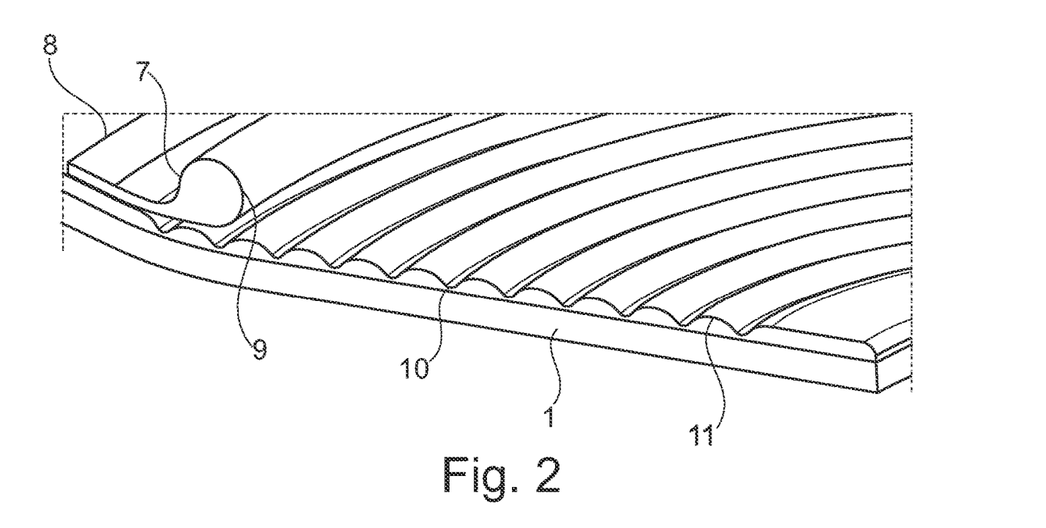
In FIG. 2 is shown a cross-section of one embodiment of an adaptable base plate, In FIGS. 3a and 3b is shown one embodiment of an adaptable base plate with a coupling for a collection bag, In FIG. 4 is shown a cross section of one embodiment of an adaptable base plate being inverted.

In FIG. 2 is shown a cross section of a first central portion of a base plate with a reinforcing structure 7 in the form of a ring of stiffer material. A collection bag may be attached to the base plate (not shown). The proximal surface is provided with a top film and a distal first layer of adhesive and a proximal second layer of adhesive. The reinforcement ring 7 comprises an outer edge 8 and an inner edge 9, the ring being attached to the top film along the outer edge 9. The inner edge 9 of the reinforcement ring is unattached to the top film allowing the part of the base plate being underneath the inner edge 9 of the ring to move independently of the reinforcement ring. The first section 1 of the base plate is provided with undulations in the form of concentric valleys 10 at least partly extending into the first adhesive and ridges 11. The undulations may be distributed homogenously such as shown in FIG. 2, where the height and width of the ridges and valleys are the same or the undulations may comprise valleys and/or ridges of different dimensions.

Figure 3A:
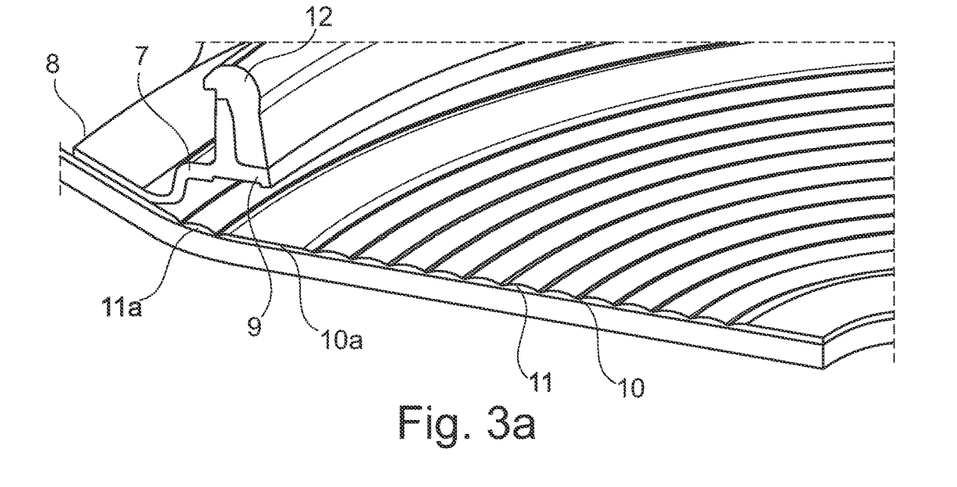
Figure 3B:
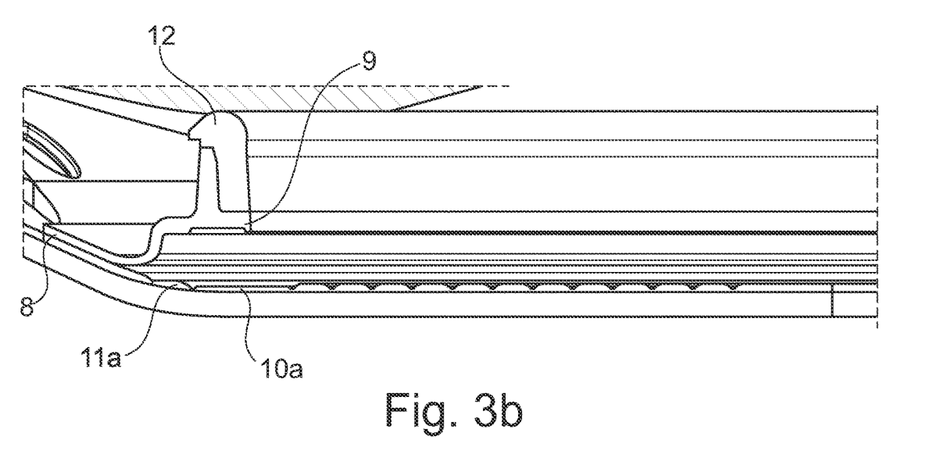

In FIGS. 3a and 3b is shown another embodiment where the reinforcement ring 7 is combined and integrated with a coupling 12 for attachment of a collection bag and where one ridge 11a is present under the ring, followed by a very broad lower ridge 10a, the broad lower ridge 10a extending further radially inwards than the ring, thus it extends further radially inwards than the inner edge 9 of the ring.

Figure 4:
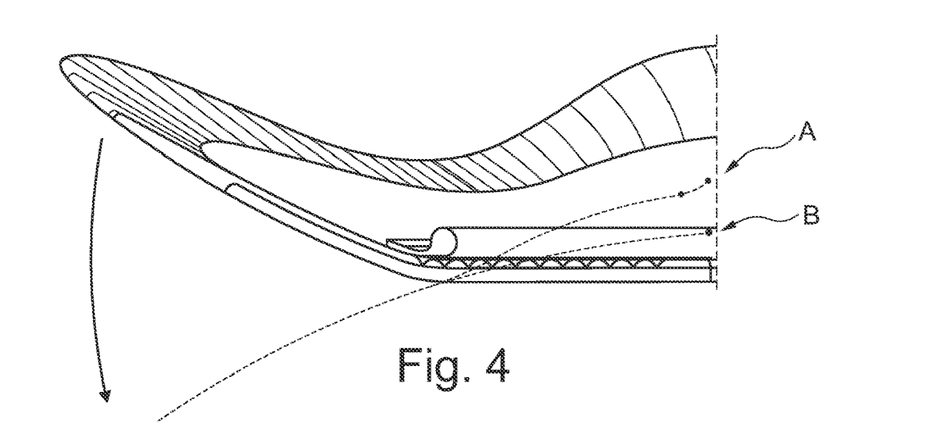

In FIGS. 4a and 4b is shown a cross section of a base plate with an indication of how it will look in the inverted position. Line A indicates the configuration of a base plate without undulations after being inverted, whereas line B indicates the same for a base plate with undulations. As can be seen, the inner boundary of the base plate raises in the plate without undulations whereas the plate with undulations will follow the skin.

Example

In a particular example of the adaptable ostomy base plate, the following materials, dimensions and process parameters are applied:

The flexible top film is a non-stretched, three-layer laminate wherein the distal-most layer is a blend of Elvax® 3190 and Orevac® 18360; the middle layer is a blend of Elvax® 3190, Elastollan® 890 and Elastollan® 978; the proximal layer is a blend of Elvax® 3190, Elastollan® 890 and Elastollan® 978. The distal and proximal layers additionally comprise a minor amount of slip agent according to the invention. The thickness of the flexible top film is 40 µm.

A first elastic skin-friendly adhesive according to the invention is provided on the proximal surface of the flexible top film in an area or zone corresponding to the first section of the base plate. The thickness of the first elastic skin-friendly adhesive in the not undulated areas is approximately 1600 µm (subject to negligible production variations). A single release liner is provided on the proximal adhesive surface of the base plate. The release liner has a thickness of 80 µm. This blank was embossed and cut into base plates with undulations in the form of ridges and valleys. The thickness of the adhesive at the ridges was 1.6 mm whereas the thickness of the valleys was 1.2 mm. The distance between the ridges was 1.6 mm. The area of the base plate being to be under the reinforcement ring was provided with a valley having a width of 4.5 mm and a thickness of 1.45 mm.

In the example, the first section is substantially planar whereas the second section have a substantially convex shape. To obtain the substantially convex shape, the ostomy base plate blank (flexible top film+adhesives+release liner) as defined above is pre-heated at 150° C. for 28 seconds and then formed in a vacuum-forming machine with a moulding tool provided with a planar and a convex section. The depth of the convexity in the moulding tool is 12 mm. After convex forming of the adhesive plate the reinforcement ring is welded on to the top film. A pre-defined stoma receiving through-going hole (size e.g. 025 mm) is punched in the ostomy base plate blank after the vacuum-forming.

In the example, the ostomy base plate has a star shaped outline with radially extending petals having an apex. The overall diameter (measured at the apex the petals) is 0100 mm.

Methods

Determination of Water Absorption

In order to get better correlation between measured water absorption and actual performance in a humanlike environment, a modified version of the ISO 62 standard was used: Pieces of adhesive of 1×25×25 mm$^3$ were fastened on a piece of glass using double sided adhesive and the constructs were immersed in saline water (0.9% NaCl in dematerialized water) at 32° C. After 24 hours the samples were removed and carefully dripped dry and weighed. The change in weight was recorded and reported as weight gain in percent of the original dry weight of the adhesive. In the following, we will call this value $w_{24h}$.

Determination of G*

The parameter G* or complex modulus as defined in "Dynamics of polymeric liquids", Vol. 1, sec. ed. 1987, Bird, Armstrong and Hassager, John Wiley and Sons Inc., was used as a measure of the hardness of an adhesive. G* at 32° C. and 0.01 Hz was measured as follows: A plate of adhesive material was pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurement was carried out at 32° C.

Determination of Softness of Backing Layer

For measuring softness of the adhesive base plate, the testing guidelines from standard ISO527-1 were used. However, the parameters defined in ISO527-1 are in itself not sufficient to exactly describe the relevant parameters for ostomy devices. An ostomy device is placed on the stomach, on skin that can easily deform more than 20%. The relevant deformation for a soft adhesive base plate with a soft top film is in the same magnitude and we have therefore defined softness (modulus) of adhesive base plates as the force in Newton at 20% deformation divided by initial sample width. We used 'dog-bone' test specimens similar to the ones described in ISO 527-2 FIG. 1, but with different dimensions to accommodate the fact that some adhesive base plates are too small to be tested with ISO 527-1. We used test samples that scale with the samples from ISO527.2 FIG. 1, but where the width $b_1$ of the narrow portion was 4 mm and Gauge length $L_0$ was 10 mm. Relative deformation ε was calculated as the absolute deformation ΔL divided by the initial length $L_0$ as described in ISO 527-1. The rate of deformation was set to 1 mm/s. To accommodate for the fact that most films are isotropic, samples were measured in the softest direction. The obtained values are averages of at least 3 measurements.

The invention claimed is:

1. An ostomy base plate comprising:
a film adapted to elongate in a range from 250% to 700%;
an adhesive composition deposited on a proximal surface of the film, with the adhesive composition adapted to adhere to skin around a stoma;
a hole formed through the film and the adhesive composition, where the hole is adapted for placement around the stoma; and
a reinforcement ring connected to a distal surface of the film;
wherein the ostomy base plate comprises a first section surrounded by a second section, with the first section extending in a radial direction between the hole and the second section, and the second section extending in the radial direction from the first section to an outer boundary of the ostomy base plate;
wherein the film in the first section of the ostomy base plate comprises undulations formed in the film and into the adhesive composition to provide the adhesive composition in the first section of the ostomy base plate with valleys of relatively lower adhesive thickness and ridges of relatively higher adhesive thickness.

2. The ostomy base plate of claim 1, wherein the adhesive composition comprises a first layer of adhesive deposited on the proximal surface of the film and a second layer of adhesive deposited on a proximal side of the first layer of adhesive.

3. The ostomy base plate of claim 1, wherein the adhesive composition comprises a first layer of adhesive deposited on the proximal surface of the film and a second layer of adhesive deposited on a proximal side of the first layer of adhesive, with the second layer of adhesive adapted to absorb moisture and the first layer of adhesive adapted to absorb less moisture than the second layer of adhesive.

4. The ostomy base plate of claim 1, wherein the adhesive composition comprises a first layer of adhesive deposited on the proximal surface of the film and a second layer of adhesive deposited on a proximal side of the first layer of adhesive, with the second layer of adhesive adapted to absorb moisture and the first layer of adhesive adapted to not absorb moisture.

5. The ostomy base plate of claim 1, wherein the undulations are concentric undulations formed in the film and into the adhesive composition.

6. The ostomy base plate of claim 1, wherein the reinforcement ring extends between an outer edge and an inner edge, with the outer edge connected to the distal surface of the film and the inner edge unattached to the film to configure a portion of the ostomy base plate under the inner edge of the reinforcement ring to move independently from the outer edge of the reinforcement ring.

7. The ostomy base plate of claim 1, wherein the undulations formed in the film in the first section of the ostomy base plate extend to a location under and proximal to the reinforcement ring.

8. The ostomy base plate of claim 1, wherein the reinforcement ring comprises a coupling surface configured to couple with a waste collecting bag.

9. The ostomy base plate of claim 1, wherein a proximal side of the adhesive composition along the first section of the ostomy base plate is substantially planar.

10. The ostomy base plate of claim 1, wherein the outer boundary of the ostomy base plate comprises a plurality of petals extending radially away from the first section, with a bridge formed between adjacent petals of the plurality of petals.

11. The ostomy base plate of claim 1, wherein a distal side of the second section of the ostomy base plate comprises radially extending embossed lines that extend to the outer boundary of the ostomy base plate.

12. An ostomy base plate comprising:
an elastic film adapted to elongate in a range from 250% to 700%;
an adhesive composition deposited on a proximal surface of the film, with the adhesive composition having a proximal side adapted to adhere to skin around a stoma; and
a hole formed through the film and the adhesive composition, where the hole is adapted for placement around the stoma;
wherein the ostomy base plate comprises a first section surrounded by a second section, with the first section extending in a radial direction between the hole and the second section, and the second section extending in the radial direction from the first section to an outer boundary of the ostomy base plate;

wherein the film in the first section of the ostomy base plate comprises undulations formed in the film and into the adhesive composition to provide the adhesive composition in the first section of the ostomy base plate with valleys of relatively lower adhesive thickness and ridges of relatively higher adhesive thickness wherein the ostomy base plate is provided to a user in a storage configuration with the proximal side of the adhesive composition in a substantially convex shape, and the undulations allow the elastic film to stretch to resist movement of the adhesive composition away from the skin around the stoma when the proximal side of the adhesive composition is inverted from the substantially convex shape to a substantially concave shape during attachment of the ostomy base plate to the skin around the stoma.

13. The ostomy base plate of claim 12, further comprising:

a reinforcement ring connected to a distal surface of the film.

\* \* \* \* \*